US010219727B2

(12) United States Patent
Krueger et al.

(10) Patent No.: US 10,219,727 B2
(45) Date of Patent: Mar. 5, 2019

(54) METHOD AND APPARATUS FOR FITTING A HEARING DEVICE

(71) Applicant: SONOVA AG, Staefa (CH)

(72) Inventors: Harald Krueger, Affoltern a.A. (CH); Juliane Raether, Mannedorf (CH); Silvia Allegro-Baumann, Unterageri (CH); Julia Rehmann, Uznach (CH); Timo Boeld, Staefa (CH)

(73) Assignee: Sonova AG, Staefa (CH)

( * ) Notice: Subject to any disclaimer, the term of this patent is extended or adjusted under 35 U.S.C. 154(b) by 317 days.

(21) Appl. No.: 15/104,484

(22) PCT Filed: Dec. 16, 2013

(86) PCT No.: PCT/EP2013/076748
§ 371 (c)(1),
(2) Date: Jun. 14, 2016

(87) PCT Pub. No.: WO2015/090352
PCT Pub. Date: Jun. 25, 2015

(65) Prior Publication Data
US 2016/0324448 A1 Nov. 10, 2016

(51) Int. Cl.
*H04R 25/00* (2006.01)
*A61B 5/12* (2006.01)

(52) U.S. Cl.
CPC .......... *A61B 5/121* (2013.01); *H04R 25/353* (2013.01); *H04R 25/70* (2013.01); *H04R 25/356* (2013.01); *H04R 2225/43* (2013.01)

(58) Field of Classification Search
CPC ......... A61B 5/121; A61B 5/123; A61B 5/125; H04R 25/353; H04R 25/502; H04R 25/505; H04R 25/70; H04R 2225/43
See application file for complete search history.

(56) References Cited

U.S. PATENT DOCUMENTS 7,082,205 B1 * 7/2006 Westermann ........ H04R 25/305
381/312
7,248,711 B2 * 7/2007 Allegro ................ H04R 25/353
381/316
(Continued)

FOREIGN PATENT DOCUMENTS

AU 2002300314 2/2004
DE 4338215 5/1995
(Continued)

OTHER PUBLICATIONS

International Search Report and Written Opinion received in International Application No. PCT/US2013/076748, dated Aug. 26, 2014.

*Primary Examiner* — Joshua Kaufman
(74) *Attorney, Agent, or Firm* — ALG Intellectual Property, LLC

(57) ABSTRACT

A method for fitting a hearing device to the needs and preferences of a user of the hearing device is disclosed. In a first step of the disclosed method, a first range for a parameter setting of a first parameter is determined based on a first audiological test performed with the user. In a second step of the disclosed method, the first parameter is adjusted to a first final parameter setting within the first range and/or a second parameter of the hearing device is adjusted to a second final parameter setting based on a second audiological test performed with the user. The second parameter is functionally related to the first parameter such that the first parameter is expressible as a function of the second parameter, and the adjusting is performed such that the first parameter setting remains within the first range. Additionally, corresponding fitting apparatuses and computer-readable media are disclosed.

20 Claims, 2 Drawing Sheets

(56) References Cited

U.S. PATENT DOCUMENTS

| | | | |
|---|---|---|---|
| 8,838,250 B2 * | 9/2014 | Botros | A61N 1/36 607/57 |
| 9,467,789 B1 * | 10/2016 | Zhao | H04R 25/70 |
| 2010/0202625 A1 * | 8/2010 | Boretzki | H04R 25/70 381/60 |
| 2011/0022119 A1 * | 1/2011 | Parker | H04R 25/70 607/56 |
| 2011/0046511 A1 * | 2/2011 | Koo | A61B 5/121 600/559 |
| 2012/0288107 A1 * | 11/2012 | Lamm | H04R 25/30 381/59 |
| 2013/0230182 A1 * | 9/2013 | Hannemann | H04R 25/30 381/60 |
| 2014/0119583 A1 * | 5/2014 | Valentine | H04R 25/70 381/316 |
| 2016/0150330 A1 * | 5/2016 | Niederberger | A61F 2/08 381/314 |
| 2016/0324448 A1 * | 11/2016 | Krueger | H04R 25/353 |

FOREIGN PATENT DOCUMENTS

| | | |
|---|---|---|
| EP | 1686566 | 8/2006 |
| EP | 2182742 | 5/2010 |
| WO | WO-2007/000161 | 1/2007 |
| WO | WO-2009/103823 | 8/2009 |
| WO | WO-2012/175134 | 12/2012 |

* cited by examiner

METHOD AND APPARATUS FOR FITTING A HEARING DEVICE

TECHNICAL FIELD

The present invention is related to a method for fitting a hearing device as well as to an apparatus capable of performing the method and to a use of the method. The present invention is especially suitable for fitting hearing devices featuring at least two mutually dependent adjustable parameters, such as a hearing device comprising a frequency transposition means.

BACKGROUND OF THE INVENTION

Hearing devices such as hearing aids (also referred to as hearing prostheses or hearing instruments) for hard of hearing people or hearing enhancement devices for augmenting the hearing capability of normal hearing persons, as well as hearing protection devices designed to prevent noise-induced hearing loss, usually comprise an input transducer, such as a microphone, for picking up sound from the surroundings, a signal processing unit for processing the signal from the input transducer, and an output transducer for converting the processed signal into a signal perceivable by the user of the hearing device. Thereby, the hearing device may either be worn at the ear (e.g. a behind-the-ear hearing device) or within the ear canal (e.g. an in-the-ear or in-canal hearing device), or alternatively be anchored in the scull (e.g. a bone-anchored hearing aid, BAHA) or implanted in the middle or inner ear (e.g. a direct acoustic cochlear stimulation, DACS, or cochlear implant). Such hearing devices need to be tailored to the specific needs and preferences of a user of the hearing device, for instance the signal processing parameters of the signal processing unit need to adjusted to the individual hearing requirements of the user, e.g. dependent on the user's specific hearing capability, such as hearing loss at different audio frequencies. Typically, a plurality of interdependent signal processing parameters needs to be adjusted in order to optimise the hearing performance achievable by the user with the help of the hearing device. This parameter adjustment process, which is commonly referred to as "fitting" process conducted by a hearing device specialist commonly referred to as "fitter", is a very complex and time-consuming procedure, which requires a lot of experience in order to achieve a satisfactory result. Fitting is often a very tedious process based on trial and error, especially when a large number of interrelated settings need to adjusted. Typically, the sequence in which the individual settings are adjusted is rather ad hoc and the optimisation process is long and weary requiring multiple iterations, where each setting is re-adjusted and fine-tuned several times over, in order to reach a "globally" optimal result.

SUMMARY OF THE INVENTION

It is an object of the present invention to provide a systematic and efficient method for fitting hearing devices featuring one or more adjustable parameters. This object is reached by the fitting method according to claim 1. Specific embodiments of the proposed method are provided in the dependent claims 2 to 10.

It is a further object of the present invention to provide a specific use of the proposed method. Such a use is given in claim 11.

It is a further object of the present invention to provide a fitting apparatus capable of performing the proposed method. Such a fitting apparatus is specified in claim 12.

Moreover, a computer program product and a computer-readable medium, respectively, comprising program code adapted to cause a computer to perform the steps of the proposed method are given in claims 13 and 14, respectively.

The present invention is first directed to a method for fitting a hearing device to the individual needs and preferences of a user of the hearing device by adjusting one or more parameters $p_1$, $p_2$ of the hearing device, comprising the steps of:

i) determining based on a first audiological test performed with the user of the hearing device a first range $[p_{1,min}, p_{1,max}]$ for a parameter setting of a first parameter $p_1$;

ii) adjusting based on a second audiological test performed with the user of the hearing device a second parameter $p_2$ to a second final parameter setting $p_{2,final}$ and/or the first parameter $p_1$ to a first final parameter setting $p_{1,final}$, wherein the first final parameter setting $p_{1,final}$ is maintained within the first range $[p_{1,min}, p_{1,max}]$, and/or wherein step ii) is carried out such that the parameter setting of the first parameter $p_1$ remains with within the first range $[p_{1,min}, p_{1,max}]$.

The proposed method may also be employed to adjust only a single parameter using two different audiological tests each one of which allows to optimise the hearing performance of the hearing device user regarding a different aspect, such as for instance phoneme distinction, fricative distinction or vowel distinction.

In an embodiment of the method the first parameter $p_1$ is functionally related to the second parameters $p_2$, such as $p_1 = f_1(p_2)$. While this functional relation directly couples the two parameters $p_1$ and $p_2$, also other relationships providing a more "loose" coupling of the two parameters $p_1$ and $p_2$ are possible. For example the following relations could define such a coupling:

$$p1 > f_2(p2);$$

$$p1 < f_3(p2);$$

$$|p1-p2| < c, \text{ where } c \text{ is a constant}.$$

In a further embodiment, the method further comprises the step of determining a second range $[p_{2,min}, p_{2,max}]$ for a parameter setting of the second parameter $p_2$ in dependence of the first range $[p_{1,min}, p_{1,max}]$.

In a further embodiment of the method the first and the second audiological test are different audiological tests.

In a further embodiment of the method the first and/or the second audiological test is an experience test, also referred to as a perceptive measure, or a performance test, also referred to as a hearing test.

An example for an experience test is the multi-stimulus test with hidden reference and anchor, also referred to as MUSHRA test. An example for a performance test is the Oldenburg sentence test (OLSA test).

In a further embodiment of the method the first and/or the second audiological test is one of:
the MUSHRA test;
the Phonak phoneme test;
a phoneme detection test;
a phoneme distinction test;
a phoneme recognition test;
a speech test, in particular a speech-in-noise test;
the Oldenburg sentence test, i.e. the OLSA test;

the Freiburger test.

In a further embodiment of the method the first and/or the second audiological test comprises the steps of:
- adjusting the first parameter $p_1$ and/or the second parameter $p_2$ to a first and/or second parameter setting to be evaluated;
- presenting a sound or other auditory stimulus to the user of the hearing device;
- obtaining a response from the user of the hearing device regarding the sound or other auditory stimulus;
- deriving a test result for the first and/or second parameter setting based on the obtained response.

In a further embodiment of the method the first and/or second parameter is one of:
- a cut-off frequency CF;
- a compression ration CR;

of a frequency transposition means of the hearing device.

In a further embodiment of the method the first and/or second audiological test is a fricative distinction test, and in particular the fricative distinction test is employed for setting the compression ratio CR.

In a further embodiment the method further comprises the step of selecting the first audiological test in dependence of the first parameter $p_1$ to be adjusted and/or selecting the second audiological test in dependence of the second parameter $p_2$ to be adjusted.

It is expressly pointed out that the above-mentioned embodiments can be arbitrarily combined to yield further specific embodiments of the method according to the present invention.

Furthermore, the present invention is directed to a use of the proposed method for fitting a hearing device adapted to perform frequency transposition processing.

Moreover, the present invention is directed to a fitting apparatus structured and configured, i.e. adapted for performing the proposed method.

In a further aspect, the present invention is directed to a computer program product comprising program code adapted to cause a computer to perform the steps according to the proposed method.

Finally, the present invention is directed to a computer-readable medium comprising program code adapted to cause a computer to perform the steps according to the proposed method.

BRIEF DESCRIPTION OF THE DRAWINGS

The present invention will now be further illustrated by way of exemplified embodiments shown in the accompanying drawings and described in detail in the following. It is pointed out that these embodiments are for illustrative purposes only and shall not limit the present invention as set out by the claims.

DETAILED DESCRIPTION OF THE INVENTION

Figure 1:
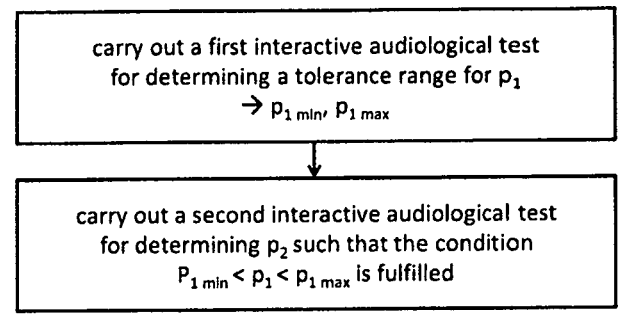
FIG. 1 shows a simple block diagram of the method according to the present invention for adjusting two parameters $p_1$ and $p_2$.

The present invention provides a systematic, general approach for fitting hearing devices featuring two or more mutually dependent parameters $p_1$ and $p_2$. The concept underlying the present invention is realised by subdividing the fitting procedure into two major steps. In the first step an appropriate range $[p_{1,min}, p_{1,max}]$ for a first parameter $p_1$ is determined with the help of a first interactive audiological test performed with the hearing device user. With this first audiological test it is ensured that the hearing performance is sufficiently good for any setting of the first parameter $p_1$ within the range $[p_{1,min}, p_{1,max}]$. Subsequently, in a second step a second parameter $p_2$ is adjusted to a final value with the aid of a second interactive audiological test performed with the hearing device user, whereby the adjustment of the value of the second parameter $p_2$ is carried out such that the first parameter $p_1$ remains within the previously determined parameter range $[p_{1,min}, p_{1,max}]$ for the first parameter $p_1$. By ensuring that the first parameter $p_1$ remains within the parameter range $[p_{1,min}, p_{1,max}]$ whilst adjusting the second parameter $p_2$, which influences the setting of the first parameter $p_1$ due to the functional relationship between $p_2$ and $p_1$ (e.g. $p_1=f(p_2)$), it is guaranteed that the hearing performance is not below the level established during the first step. Based on the functional relationship between $p_1$ and $p_2$ a range $[p_{2,min}, p_{2,max}]$ for the second parameter $p_2$ can be determined, within which the second parameter $p_2$ is then adjusted during the second step until a sufficient hearing performance is established based on the second audiological test. With this two-step procedure as schematically depicted in FIG. 1 both mutually dependent parameters $p_1$ and $p_2$ can be optimised in a systematic and efficient manner yielding an individually fitted hearing device, which provides the desired hearing performance for a specific user. The proposed fitting method thus allows to achieve a globally (versus locally as conventionally obtained) optimised hearing device settings, i.e. a hearing device fitting is provided where certain desired levels of hearing performance as determined by the employed audiological tests are satisfied.

In the following the fitting method according to the present invention is exemplified for a hearing device capable of performing frequency transposition processing. Hereby the term "transposition" or "transpose" is defined as having at least one of the following meanings:
- a replacement of destination/target frequency components by source frequency components;
- any combination of destination/target frequency components with corresponding source frequency components.

Various approaches for frequency lowering have been pursued so that hearing impaired users with a high frequency hearing loss can benefit, especially in those cases where an amplification of the original high frequency sound is not useful, e.g. due to dead regions, or not possible, e.g. due to potential feedback problems when applying high gain or due to a limited bandwidth of the applied gain. Known frequency lowering schemes are for instance disclosed in WO 2007/000161 A1, U.S. Pat. No. 7,248,711 B2, AU 2002300314 A1, EP 1 686 566 A2 and WO 2012/175134 A1. In the frequency transposition scheme described in AU 2002300314 A1 two parameters need to be adjusted, namely a cut-off frequency CF and a compression ratio CR.

Figure 2:
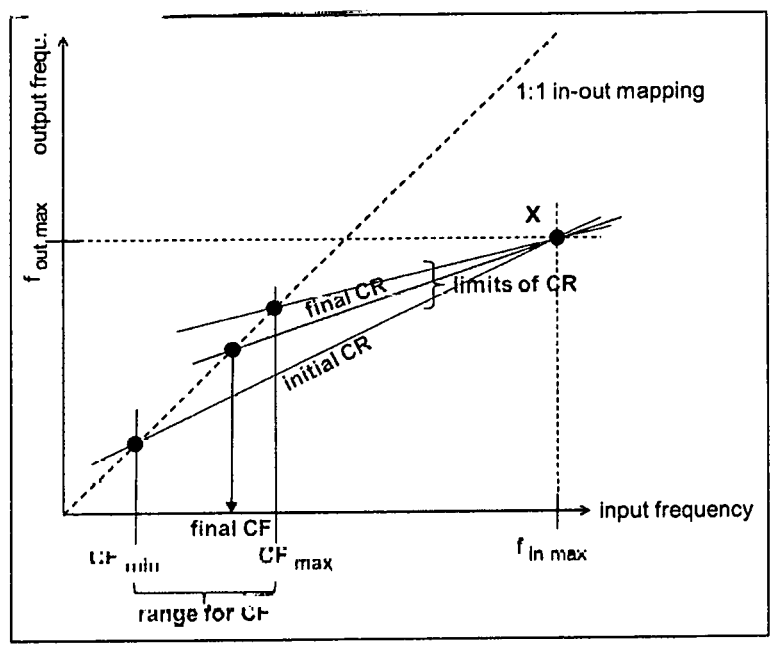
FIG. 2 shows a graph depicting a known transposition scheme to illustrate the application of the method according to the present invention to a hearing device comprising a frequency transposition means with the two adjustable parameters cut-off frequency CF and compression ratio CR.

FIG. 2 depicts a graph illustrating the mapping of input frequencies (assigned to the horizontal axis) to output frequencies (assigned to the vertical axis). When applying the frequency transposition scheme provided in AU 2002300314 A1 no frequency compression is applied below the cut-off frequency CF and a frequency compression with a compression ratio CR is applied above the cut-off frequency CF up to the maximum input frequency $f_{in,max}$. $f_{in,max}$ is the maximum input frequency to be processed, and $f_{out,max}$ is the maximum output frequency perceivable by the hearing device user for whom the hearing device is to be fitted. $f_{out,max}$ is a function of the user's audiogram. These two frequencies define the point "X" in the input-output frequency diagram illustrated in FIG. 2. In the first step of the fitting procedure, the lowest cut-off frequency $CF_{min}$ for which acceptable vowel sound quality (=a specific aspect of hearing performance) is obtained is determined for example with the help of MUSHRA testing. Optionally, also vowel distinction may be evaluated. Evaluation of vowel sound quality is only performed at frequencies below $f_{out,max}$ with the hearing device user. The test results yield $CF_{min}$ as the lower boundary of the cut-off frequency range. Then for instance a pre-defined frequency value, e.g. 320 Hz, is added to the determined $CF_{min}$ yielding an upper boundary $CF_{max}$ of the cut-off frequency range. $CF_{max}$ could also be set in dependence of $f_{out,max}$, for example $CF_{max}=f_{out,max}$. $CF_{max}$ could also be determined by the aforementioned audiological test, as the frequency above which the result of a vowel distinction test performed with the hearing device user does not show a significant improvement upon increasing the cut-off frequency CF. In the second step of the fitting procedure an initial value for the compression ration CR is determined by connecting the point "X" in the input-output frequency diagram with the intersection of the lower boundary $CF_{min}$ of the cut-off frequency range with the 1:1 input-output mapping line. With this setting of the compression ratio CR the fricative distinction is evaluated, e.g. by means of the Phonak phoneme test. The initial compression ratio setting is now increased in small steps until the fricative distinction becomes unacceptable. Note that the evaluated compression ratio settings must remain within the limits set by the range [$CR_{min}$, $CR_{max}$] for cut-off frequency CR as established previously in step 1. The finally determined compression ratio setting "final CR" ($CR_{final}$) in turn sets the final value for the cut-off frequency setting "final CF" ($CF_{final}$) within the previously defined cut-off frequency range [$CR_{min}$, $CR_{max}$].

Figure 3:
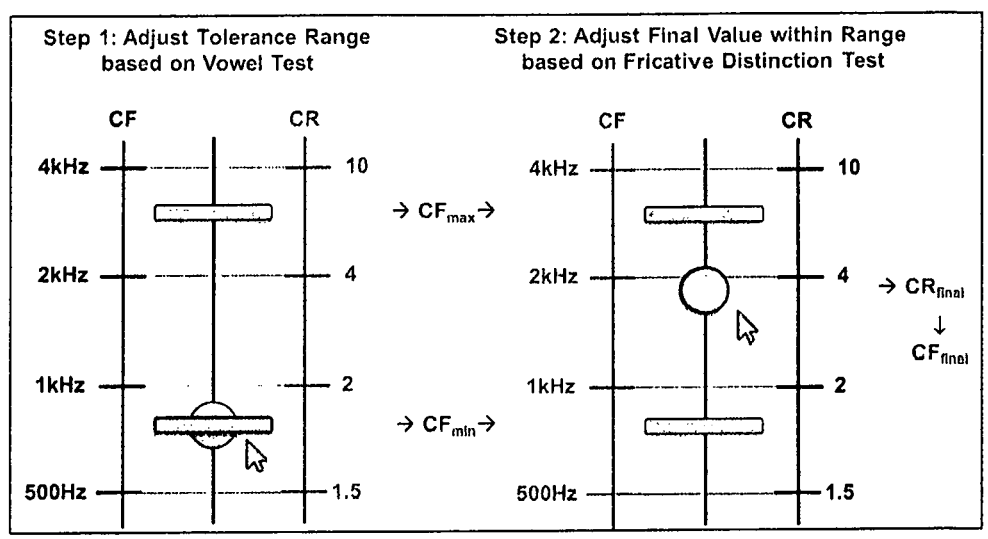
FIG. 3 shows an exemplary graphical user interface (GUI) forming part of a fitting apparatus according to the present invention, whereby the GUI comprises a slider for simultaneously adjusting the two parameters cut-off frequency CF and compression ratio CR and is adapted to perform the method according to the present invention.

An exemplary GUI for fitting the two dependent parameters of the described frequency lowering scheme is shown in FIG. 3. The parameters cut-off frequency CF and compression ratio CR that need to be adjusted are functionally coupled. Accordingly, the GUI consists of two scales for cut-off frequency CF and compression ratio CR each having three sliding elements for setting the tolerance range (i.e. upper and lower boundary) and the final value of the parameter. The left side shows the step of adjusting the tolerance range for the first parameter, i.e. the cut-off frequency CF, determined during step 1 of the fitting procedure. The right side shows the step of setting the final value of the second parameter, i.e. the compression ratio CR, determined in step 2 of the procedure. Note that $CR_{final}$ in turn fixes $CF_{final}$ within the previously established tolerance range [$CF_{min}$, $CF_{max}$] for the cut-off frequency CF. The "tolerance" range signifies the parameter range for a certain adjustable parameter within which a desired hearing performance is achieved.

The proposed scheme is also applicable in those cases where more than two mutually dependent parameters need to be adjusted. The described two-step adjustment process is then extended to all further parameters. Thereby, adjustments made to a further parameter are constrained such that the ensued adjusted setting of another parameter with which the further parameter is functionally related remains within a previously established range. The additional execution of the two-step procedure may require further audiological tests (e.g. pertaining to further aspects of hearing performance such as vowel recognition, consonant recognition, word recognition, speech recognition, musical tone recognition, timbre recognition, etc.). The "first steps" always have a parameter range as a result, and the "second steps" set the final values of one or more parameters. The method will require at least one first step and one second step. An appropriate GUI would typically have a scale with e.g. three sliders or another input means for the execution of each of the stated steps.

The invention claimed is:

1. A method for fitting a hearing device to a user of the hearing device, the method comprising:
    determining, based on a first audiological test performed with the user of the hearing device, a first range for a parameter setting of a first parameter of the hearing device; and
    adjusting, based on a second audiological test performed with the user of the hearing device and different from the first audiological test,
        the first parameter to a first final parameter setting within the first range, and
        a second parameter of the hearing device to a second final parameter setting, the second parameter functionally related to the first parameter such that the first parameter is expressible as a function of the second parameter;
    wherein the adjusting is performed such that the parameter setting of the first parameter remains within the first range.

2. The method of claim 1, further comprising determining, based on the first range, a second range for a parameter setting of the second parameter.

3. The method of claim 1, wherein:
    the first audiological test is at least one of an experience test and a performance test; and
    the second audiological test is at least one of an experience test and a performance test.

4. The method of claim 1, wherein:
    the first audiological test comprises at least one of a multiple-stimulus test with hidden reference and anchor ("MUSHRA test"), a Phonak phoneme test, a phoneme detection test, a phoneme distinction test, a phoneme recognition test, a speech test, a speech-in-noise test, an Oldenburg sentence test, and a Freiburger test; and
    the second audiological test comprises at least one of the MUSHRA test, the Phonak phoneme test, the phoneme detection test, the phoneme distinction test, the phoneme recognition test, the speech test, the speech-in-noise test, the Oldenburg sentence test, and the Freiburger test.

5. The method of claim 1, wherein:
    the first audiological test is performed by adjusting the first parameter to a first parameter setting to be evaluated, presenting a first sound or other auditory stimulus to the user of the hearing device, obtaining a first response from the user of the hearing device regarding the first sound or other auditory stimulus, and deriving a first test result for the first parameter setting based on the obtained first response; and the second audiological test is performed by adjusting the second parameter to a second parameter setting to be evaluated, presenting a second sound or other auditory stimulus to the user of the hearing device, obtaining a second response from the user of the hearing device regarding the second sound or other auditory stimulus, and deriving a second test result for the second parameter setting based on the obtained second response.

6. The method of claim 1, wherein:
the first parameter is one of a cut-off frequency and a compression ratio of a frequency transposition performed by the hearing device; and
the second parameter is one of the cut-off frequency and the compression ratio of the frequency transposition performed by the hearing device.

7. The method of claim 6, wherein at least one of the first audiological test and the second audiological test is a fricative distinction test, the fricative distinction test used to facilitate setting the compression ratio.

8. The method of claim 1, further comprising:
selecting the first audiological test based on the first parameter; and
selecting the second audiological test based on the second parameter.

9. A fitting apparatus for fitting a hearing device to a user of the hearing device, the fitting apparatus comprising:
at least one physical computing device that
determines, based on a first audiological test performed with the user of the hearing device, a first range for a parameter setting of a first parameter of the hearing device; and
adjusts, based on a second audiological test performed with the user of the hearing device and different from the first audiological test,
the first parameter to a first final parameter setting within the first range, and
a second parameter of the hearing device to a second final parameter setting, the second parameter functionally related to the first parameter such that the first parameter is expressible as a function of the second parameter;
wherein the at least one physical computing device performs the adjustment such that the parameter setting of the first parameter remains within the first range.

10. The fitting apparatus of claim 9, wherein the at least one physical computing device further determines, based on the first range, a second range for a parameter setting of the second parameter.

11. The fitting apparatus of claim 9, wherein:
the first audiological test is at least one of an experience test and a performance test; and
the second audiological test is at least one of an experience test and a performance test.

12. The fitting apparatus of claim 9, wherein:
the first audiological test comprises at least one of a multiple-stimulus test with hidden reference and anchor ("MUSHRA test"), a Phonak phoneme test, a phoneme detection test, a phoneme distinction test, a phoneme recognition test, a speech test, a speech-in-noise test, an Oldenburg sentence test, and a Freiburger test; and
the second audiological test comprises at least one of the MUSHRA test, the Phonak phoneme test, the phoneme detection test, the phoneme distinction test, the phoneme recognition test, the speech test, the speech-in-noise test, the Oldenburg sentence test, and the Freiburger test.

13. The fitting apparatus of claim 9, wherein:
the first audiological test is performed by adjusting the first parameter to a first parameter setting to be evaluated, presenting a first sound or other auditory stimulus to the user of the hearing device, obtaining a first response from the user of the hearing device regarding the first sound or other auditory stimulus, and deriving a first test result for the first parameter setting based on the obtained first response; and
the second audiological test is performed by adjusting the second parameter to a second parameter setting to be evaluated, presenting a second sound or other auditory stimulus to the user of the hearing device, obtaining a second response from the user of the hearing device regarding the second sound or other auditory stimulus, and deriving a second test result for the second parameter setting based on the obtained second response.

14. The fitting apparatus of claim 9, wherein:
the first parameter is one of a cut-off frequency and a compression ratio of a frequency transposition performed by the hearing device; and
the second parameter is one of the cut-off frequency and the compression ratio of the frequency transposition performed by the hearing device.

15. The fitting apparatus of claim 14, wherein at least one of the first audiological test and the second audiological test is a fricative distinction test, the fricative distinction test used to facilitate setting the compression ratio.

16. The fitting apparatus of claim 9, wherein the at least one physical computing device further:
selects the first audiological test based on the first parameter; and
selects the second audiological test based on the second parameter.

17. A non-transitory computer-readable medium comprising computer-executable instructions configured to cause at least one physical computing device to:
determine, based on a first audiological test performed with a user of a hearing device, a first range for a parameter setting of a first parameter of the hearing device; and
adjust, based on a second audiological test performed with the user of the hearing device and different from the first audiological test,
the first parameter to a first final parameter setting within the first range, and
a second parameter of the hearing device to a second final parameter setting, the second parameter functionally related to the first parameter such that the first parameter is expressible as a function of the second parameter;
wherein the at least one physical computing device performs the adjustment such that the parameter setting of the first parameter remains within the first range.

18. The non-transitory computer-readable medium of claim 17, wherein the computer-executable instructions are further configured to cause the at least one physical computing device to determine, based on the first range, a second range for a parameter setting of the second parameter.

19. The non-transitory computer-readable medium of claim 17, wherein:
the first parameter is one of a cut-off frequency and a compression ratio of a frequency transposition performed by the hearing device; and the second parameter is one of the cut-off frequency and the compression ratio of the frequency transposition performed by the hearing device.

20. The non-transitory computer-readable medium of claim 19, wherein at least one of the first audiological test and the second audiological test is a fricative distinction test, the fricative distinction test used to facilitate setting the compression ratio.

\* \* \* \* \*